US012318217B2

(12) United States Patent
Dinh et al.

(10) Patent No.: US 12,318,217 B2
(45) Date of Patent: Jun. 3, 2025

(54) ACCESSORY FOR ANALYZING PATIENT SIGNALS DURING CARDIOPULMONARY RESUSCITATION

(71) Applicant: PHYSIO-CONTROL, INC., Redmond, WA (US)

(72) Inventors: Doan Dinh, Seattle, WA (US); Tyson Taylor, Bothell, WA (US); Daniel Piraino, Seattle, WA (US); Roderick Briscoe, Carnation, WA (US)

(73) Assignee: Physio-Control, Inc., Redmond, WA (US)

( * ) Notice: Subject to any disclaimer, the term of this patent is extended or adjusted under 35 U.S.C. 154(b) by 504 days.

(21) Appl. No.: 17/034,536

(22) Filed: Sep. 28, 2020

(65) Prior Publication Data

US 2021/0093250 A1 Apr. 1, 2021

Related U.S. Application Data

(60) Provisional application No. 62/908,281, filed on Sep. 30, 2019.

(51) Int. Cl.
*A61B 5/00* (2006.01)
*A61B 5/01* (2006.01)
*A61B 5/318* (2021.01)

(52) U.S. Cl.
CPC .......... *A61B 5/4848* (2013.01); *A61B 5/0006* (2013.01); *A61B 5/0008* (2013.01); *A61B 5/01* (2013.01); *A61B 5/318* (2021.01); *A61B 2505/01* (2013.01)

(58) Field of Classification Search
CPC ..... A61B 5/4848; A61B 5/0006; A61B 5/318; A61B 5/346–367; A61B 2505/01; A61N 1/39; A61N 1/3904; A61N 1/39044; A61N 1/3912; A61N 1/3918; A61N 1/3925–395; A61N 1/3968
See application file for complete search history.

(56) References Cited

U.S. PATENT DOCUMENTS

| 6,115,627 | A | * | 9/2000 | Street | A61B 5/366 600/515 |
| 9,204,845 | B2 | | 12/2015 | Sullivan et al. | |
| 9,414,786 | B1 | * | 8/2016 | Brockway | A61B 5/0006 |
| 9,545,211 | B2 | | 1/2017 | Sullivan et al. | |

(Continued)

FOREIGN PATENT DOCUMENTS

| AU | 2003273605 A1 * | 12/2003 | ........... A61B 5/0006 |
| WO | WO-2016154425 A1 * | 9/2016 | ........... A61B 5/1118 |

*Primary Examiner* — Michael R Bloch
(74) *Attorney, Agent, or Firm* — Lee & Hayes, P.C.

(57) ABSTRACT

An accessory for a medical device, including an input configured to receive a signal from a signal source and one or more processors configured to: analyze the signal from the signal source, and determine one or more deterministic signals based on the analysis of the signal, the one or more deterministic signals configured to elicit a defined response from the medical device. The accessory also includes an output configured to transmit the one or more deterministic signals to the medical device. The accessory may be, for example, a device located in a therapy path of the medical device, a removable circuit board connected to the medical device, or connected to or a part of the signal source.

20 Claims, 5 Drawing Sheets

(56) References Cited

U.S. PATENT DOCUMENTS

| | | | | |
|---|---|---|---|---|
| 11,446,082 B2* | 9/2022 | Blanck | ............... | A61B 18/1492 |
| 2011/0213227 A1* | 9/2011 | Ziv | ........................ | A61B 5/021 |
| | | | | 600/323 |
| 2015/0257709 A1* | 9/2015 | Quan | ..................... | A61B 5/318 |
| | | | | 600/510 |
| 2015/0297107 A1* | 10/2015 | Sullivan | ................. | A61B 5/361 |
| | | | | 600/523 |

* cited by examiner

ACCESSORY FOR ANALYZING PATIENT SIGNALS DURING CARDIOPULMONARY RESUSCITATION

PRIORITY

This disclosure claims benefit of U.S. Provisional Application No. 62/908,281, titled "ACCESSORY FOR ANALYZING PATIENT SIGNALS DURING CARDIOPULMONARY RESUSCITATION," filed on Sep. 30, 2019, which is incorporated by reference herein in its entirety.

TECHNICAL FIELD

This disclosure is directed to systems and methods for an intercept or accessory device connected between a signal source and a medical device such that the intercept or accessory device analyzes a signal from the signal source and outputs a deterministic signal intended to elicit a defined response from the medical device.

BACKGROUND

Medical devices are continually being updated with new, life-saving technology. However, many medical devices, such as defibrillators, chest compression devices, etc., can often be expensive to purchase. Therefore, when new medical devices are released with updated life-saving technology, many users or rescuers do not upgrade their equipment as long as their current equipment is working properly due to the cost of the new equipment.

However, users and rescuers that do not have updated equipment have patients that may not be receiving the most recent technology in life-saving practices, which can be detrimental to the patient.

Examples of the disclosure address these and other deficiencies of the prior art.

BRIEF DESCRIPTION OF THE DRAWINGS

Aspects, features and advantages of examples of the present disclosure will become apparent from the following description of examples in reference to the appended drawings in which.

DESCRIPTION

Figure 1:
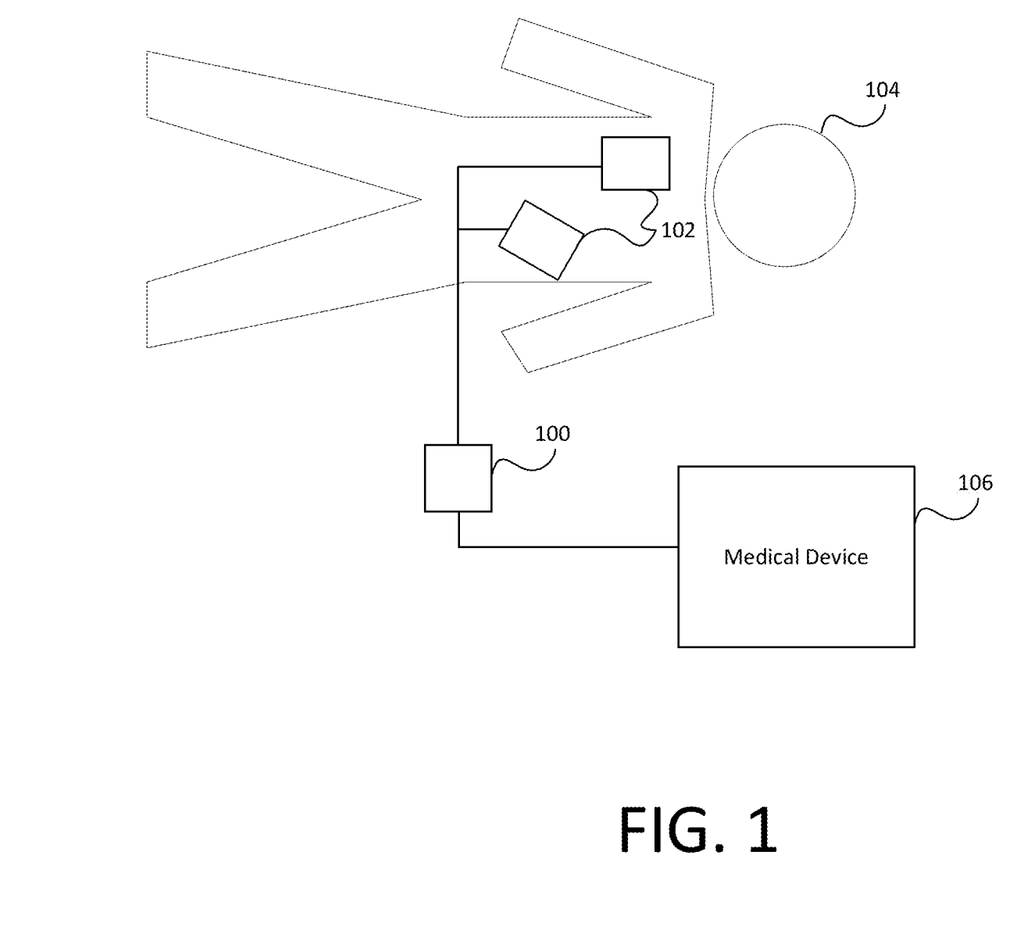
FIG. 1 is a block diagram of a rescue scene using an accessory device according to some examples of the disclosure.

FIG. 1 illustrates an example of an accessory device 100 electrically connected between a signal source 102 coupled to a patient 104 and a medical device 106. As can be seen in FIG. 1, the accessory device 100 is located between the signal source 102 and the medical device 106. As will be discussed in more detail below, the accessory device 100 receives a signal from the signal source 102. The accessory device 100 can analyze the signal from the signal source 102 and output a deterministic signal to the medical device 106 based on the analysis. The analysis performed on the signal from the signal source may be an updated analysis that is not performed by the medical device 106. For example, the analysis may include a new or improved method for filtering a signal from the signal source 102, or include a new or updated standard or procedure for analyzing the signal from the signal source 102.

The deterministic signal can elicit a response from the medical device 106 based on the new or updated analysis of the signal from the signal source 102. For example, the deterministic signal can elicit a particular response from the medical device 106, such as sending a therapy back to the patient through the connected accessory device 100 or performing any other function, such as outputting audio or visual information, storing information, selecting a therapy response, etc. As an example, a signal which could not be processed by the medical device 106 due to excessive noise, may be processed using a new or updated analysis by the accessory device 100. The accessory device 100 can then output a deterministic signal to prompt the medical device 106 to output a particular response that would have been output had the medical device 106 been capable of analyzing the signal from the signal source 102 in the same manner as the accessory device 100.

While a wired connection is shown between the signal source 102, the accessory device 100, and the medical device 106, one or both of the connections may be wireless, as will be understood by one of ordinary skill in the art.

Further, although the accessory device 100 is shown separate and connected to the medical device 106, the accessory device 100 could be a component which plugs or connects directly to the medical device, such as a removable and/or releaseable circuit board or any other removable device. That is, the accessory device 100 could be a modular unit which can connect directly to and be stored in the medical device 106.

Figure 2:
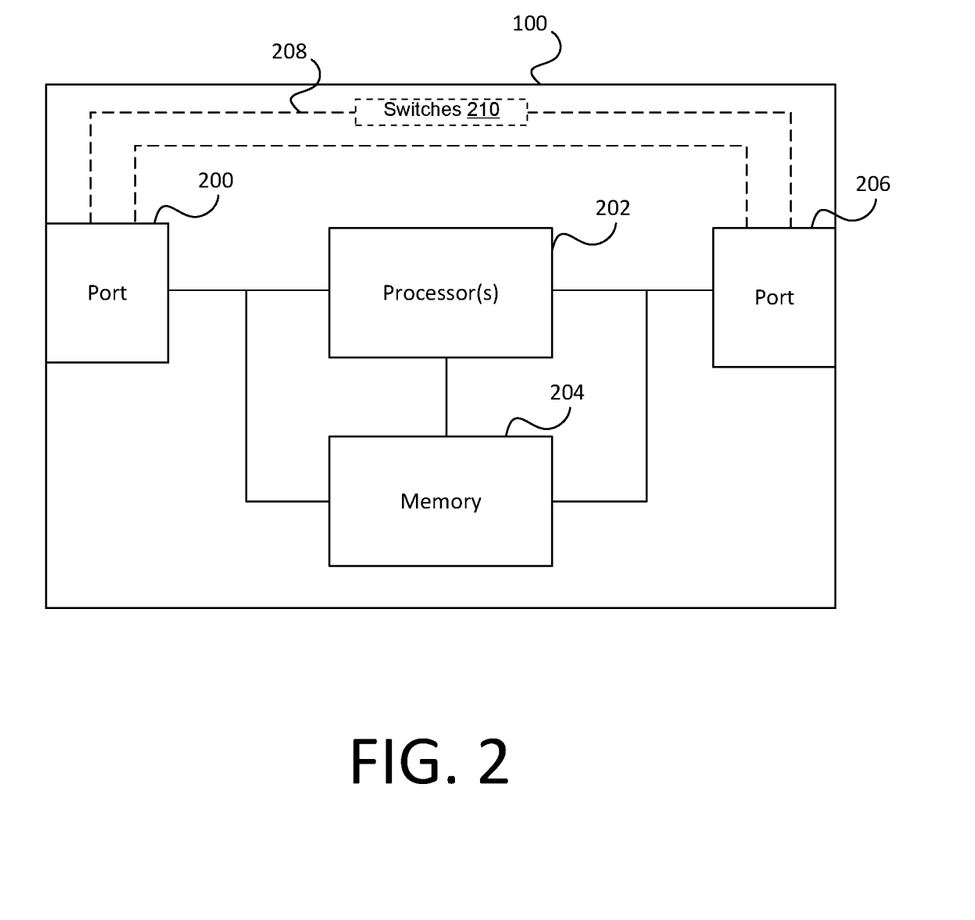
FIG. 2 is a block diagram of an accessory device according to some examples of the disclosure.

In other examples, the accessory device 100 may be included as a component of the signal source 102. For example, the accessory device 100 may be included with a defibrillation electrode or other sensor which collects data from the patient. Further, as will also be understood by one skilled in the art, the components of the accessory device 100 may not all be located on a single device. For example, the one or more processors 202 and/or the memory 204 of the accessory device 100 may be remote from the ports 200 and 202 of the accessory device. The accessory device 100 may include one or more wireless transmitters and the one or more processors 202 may be included, for example, in a cloud for performing the analysis and/or storage of data.

FIG. 2 illustrates a block diagram of an accessory device 100 according to some examples of the disclosure. The accessory device 100 includes a port 200 to receive a signal from the signal source 102. The signal source 102 may be sent to one or more processors 202 to be analyzed. As will be understood by one skilled in the art, the accessory device 100 may also include a memory 204, and other hardware within the device that electrically communicate with the one or more processors 202. The one or more processors 202 may communicate with the other hardware components, such as filters or other devices, to perform any required analysis of the received signal. The accessory device 100 also includes a port 206 to output a deterministic signal to the medical device 106 based on the analysis.

In some examples, port 200 may also output a signal to the signal sources, such as a therapy signal. Additionally or alternatively, in some examples, the accessory device 100 may also include a shielded path 208 to pass a therapy signal through the accessory device 100 without impacting the ports 200 and 206, as well as the other components of the accessory device 100, such as the one or more processors 202 and the memory 204.

Figure 3:
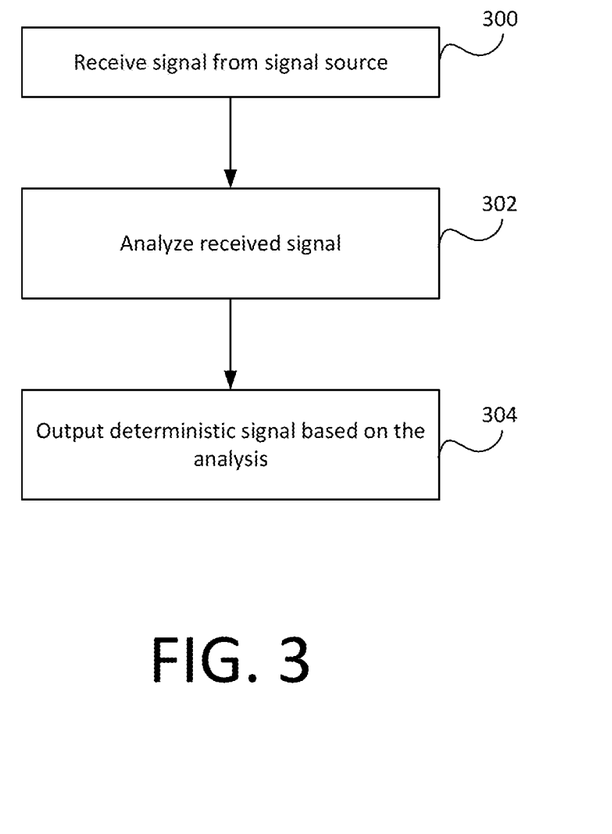
FIG. 3 is a flow chart illustrating an operation of an accessory device according to some examples of the disclosure.

FIG. 3 is a flow chart illustrating an operation of the accessory device 100. Initially, the accessory device 100 receives in operation 302 a signal from the signal source 102. The signal may be, for example, any physiological signal and/or a medical device-related signal. Examples include, but are not limited to, electrocardiogram signals, impedance signals, capnography signals, plethysmography signals, oximetry signals, pressure signals, temperature signals, and cardiopulmonary resuscitation (CPR) feedback signals.

In operation 304, the accessory device 100 analyzes the received signal from the signal source 102. The analysis may include, for example, filtering the signal or analyzing the signal in a manner not done by the medical device 106. In operation 306, a deterministic signal may then be output by the accessory device 100 to elicit a response from the medical device 106. As mentioned above, the deterministic signal is intended to elicit a defined response from the medical device 106. That is, in some examples, the deterministic signal is a conditioned signal which when received by the medical device 106 causes a particular response. For example, the deterministic output signal could be a simulated signal which causes the medical device to either act or not act in a certain manner, such as generating an alert or performing some function. In other examples, the deterministic output signal could be a filtered signal.

The medical device 106 may be any type of medical device, such as a defibrillator, radio frequency ablation system, pacemaker, chest compression system, temperature management devices, such as patient cooling or warming devices, etc.

As an example, the accessory device 100 will be described in use with a defibrillator. Using conventional defibrillators, a rescuer and/or a chest compression device must pause CPR compressions during a rhythm analysis of the defibrillator to determine if a shock is needed by the patient. That is, conventional defibrillators are unable to correctly analyze and filter at least some physiological signals which are sensed during chest compressions due to ECG signal deterioration induced by mechanical chest compressions, which will be referred to herein as compression artifacts, in the signals. However, using the accessory device 100, the accessory device 100 can receive patient physiological signals during CPR compressions and determine whether a shock is needed. The accessory device 100 can also receive patient signals with other known artifacts, such as ventilation artifacts, as discussed in, for example, U.S. Pat. No. 9,204,845 titled Filtering Patient Signal Also for Ventilation Artifacts, issued on Dec. 8, 2015, which is incorporated herein by reference in its entirety. While compressions artifacts are discussed below for ease of discussion, the accessory device 100 is not limited to filtering compression artifacts but may filter other known artifacts, such as ventilations artifacts, motion artifacts, or electrostatic artifacts. The accessory device 100 can then output deterministic signals to the defibrillator based on the analysis to cause the defibrillator either to output a therapy signal, continue monitoring, or output visual or audio information or instructions.

As shown in FIG. 1, the accessory device 100 can be included in a therapy path, between the signal source 102, which may be, for example, defibrillation electrodes, and the medical device 106, which may be a defibrillator. The accessory device 100 receives patient physiological signals from the signal source 102, such as a patient's ECG and impedance signals. As mentioned above, these signals may include compression artifacts from CPR compressions. The one or more processors 202 in the accessory device 100 analyze the received signals and outputs a deterministic signal to the defibrillator so that the defibrillator can output a response, such as a therapy signal and/or information to a user.

The deterministic signal may be, for example, a filtered or unfiltered version of the input signal or, in some examples, the deterministic signal may be a simulated signal to cause a particular response from the medical device. For example, the one or more processors 202 performs an analysis on the input signal, which may include artifacts from chest compressions, and output filtered ECG rhythm and impedance signals as the deterministic signals so that the defibrillator can use its inherent rhythm analysis to analyze the patient's rhythm and determine if a shock is necessary.

Figure 4:
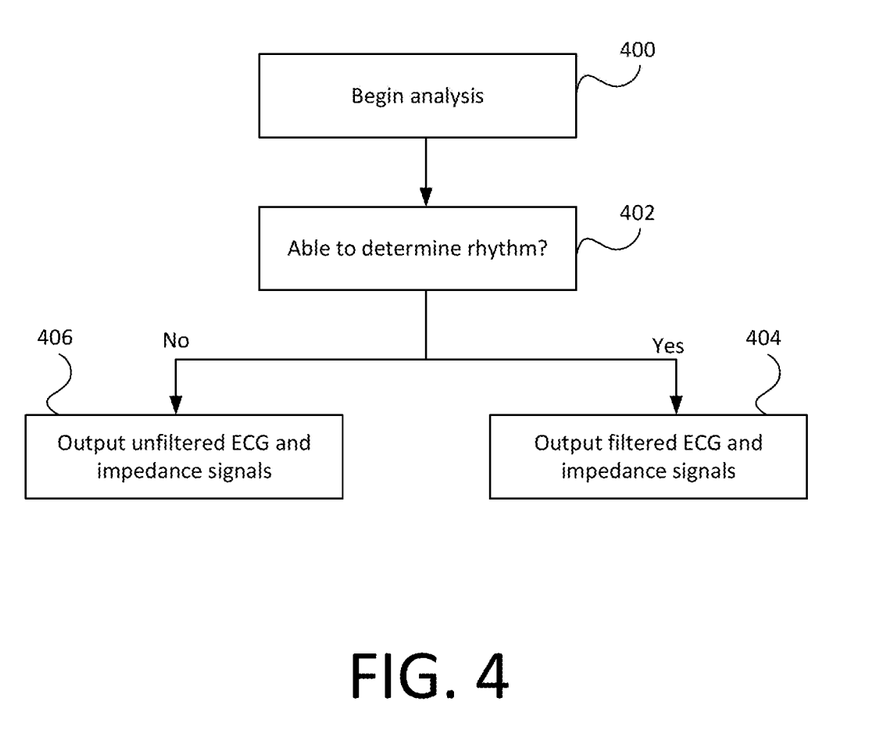
FIG. 4 is a flow chart illustrating an operation of an accessory device connected to a defibrillator according to other examples of the disclosure.

FIG. 4 illustrates an example operation of an accessory device 100 connected to a defibrillator. In operation 400, the medical device begins analysis of the received signal from the signal source 102. The received signal may include compression artifacts since the signal may be sensed during CPR compressions. In this example, the received signal includes both an ECG signal as well as an impedance signal. During the analysis, in operation 402, the one or more processors 202 determine whether a rhythm can be detected or determined based on the received signals.

If the rhythm can be detected or determined in the received signal, even with the chest compression artifacts from CPR being performed simultaneously with the analysis, then in operation 404, the one or more processors 202 can filter the ECG and impedance signals to remove the chest compression artifacts and output the filtered ECG and impedance signals to the medical device 106. An example of such filtering can be found, for example, in U.S. Pat. No. 9,545,211, titled "System and method for electrocardiogram analysis and optimization of cardiopulmonary resuscitation and therapy delivery," issued on Jan. 17, 2017. The medical device 106 may then perform its own rhythm analysis and determine if a shock is required.

However, if the rhythm cannot be detected during analysis of the received signals by the one or more processors 202 due to the compression artifacts, then the one or more processors 202 cause the unfiltered ECG and impedance signals to be output to the medical device 106 in operation 406. The unfiltered ECG and impedance signals can be detected by the medical device 106, which will cause the medical device to notify a user to stop the chest compressions for a period of time to allow the defibrillator to perform a rhythm analysis with signals not impacted by chest compressions. This is because conventional medical devices 106 are unable to analyze ECG and impedance signals with the compression artifacts, and so such medical devices 106 output an alert to the user to stop chest compressions.

In this example, since the filtered ECG and impedance signals are sent to the defibrillator when a rhythm can be detected, the defibrillator can display and store the patient's filtered signals on the defibrillation device.

Figure 5:
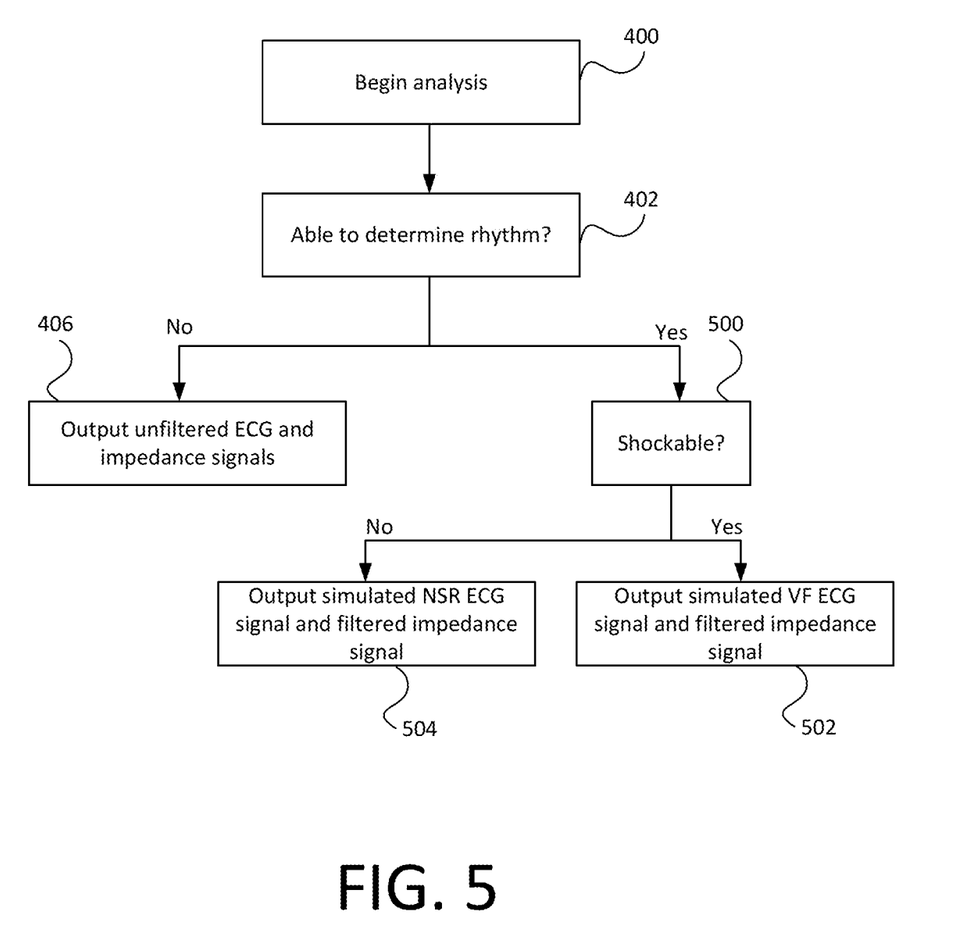
FIG. 5 is a flow chart illustrating an alternative operation of an accessory device connected to a defibrillator according to other examples of the disclosure.

FIG. 5 illustrates an alternative example operation of the accessory device 100. Operations similar to those discussed with respect to FIG. 4 performed in the operation of FIG. 5 are given the same reference numbers as shown in FIG. 4. Similar to FIG. 4, in this alternative example operation, the one or more processors 202 begin analysis in operation 400 and determine whether a rhythm is detectable in operation 402 with the compression artifacts in the ECG and impedance signals.

If the rhythm cannot be determined, then in operation 406, the one or more processors 202 will cause the unfiltered ECG and impedance signals to be sent to the medical device 106, which will cause the medical device 106 to alert the user to stop compressions to obtain a clean ECG and impedance signal while CPR compressions are not performed.

However, if in operation 402 the rhythm can be determined, then the one or more processors 202 may determine in operation 500 whether or not the rhythm is a shockable rhythm. If the rhythm is shockable, then in operation 502, the one or more processors 202 can cause the accessory device 100 to output a simulated ventricular fibrillation (VF) signal and a filtered impedance signal that is known to trigger the defibrillator to determine that a shock is advised. However, if the one or more processors 202 determine that the rhythm is not shockable, then in operation 504, the one or more processors 202 cause the accessory device 100 to output a simulated normal sinus rhythm (NSR) signal and a filtered impedance signal that is known to trigger the defibrillator to determine that a shock is not advised.

In some examples, the memory 204 of the accessory device may include data storage. In such examples, the raw or unfiltered signals received in the accessory device 100, such as physiological signals, may be stored and later retrieved post-event. This can allow for the raw data collected to be used or incorporated into post-event review data providing a complete dataset for high quality post-event review.

Further, in some examples, although not shown, the accessory device 100 may also include a display to display raw, unfiltered signals from the signal source 102 on the accessory device 100. The display and/or another output, such as a speaker, may also be used to provide instructions to a user, such as an indication on whether to continue or pause CPR, for example.

As mentioned above, the deterministic signals output by the accessory device 100 may cause the connected medical device 106, such as a defibrillator, to output a therapy signal to a patient. Since the accessory device 100 is included in the therapy path, the therapy signal from the medical device 106 would travel through the shielded path 208 of the accessory device to protect the components, such as the one or more processors 202, within the accessory device 100. High current switches 210, diodes, and other electrical components may be used in the shielded path to protect the other electrical components in the accessory device 100 from the therapy signal.

Some medical devices 106, such as conventional defibrillators, only perform shock analysis when a CPR timer has elapsed, as a conventional defibrillator can only analyze the ECG and impedance signals that do not contain compression artifacts. In some examples, the accessory device 100 may continually or repeatedly receive the signals from the signal source 102 and perform the analysis of the received signals. In such an example, the accessory device 100 continually or repeatedly outputs a deterministic signal to the electrically connected medical device 106. The medical device 106, however, may or may not analyze the received deterministic signal until the CPR timer has elapsed. Continually or repeatedly sending the deterministic signals from the accessory device 100, however, allows the medical device 106 to perform the analysis on the most up-to-date signal, without any knowledge of the accessory device 100.

Examples of the disclosure allow for medical devices 106 which may be outdated to be able to perform updated analysis without having to replace the entirety of the medical device 106. In some examples, the accessory devices 100 may be able to be updated with new procedures or analysis techniques as they are released.

Aspects of the disclosure may operate on particularly created hardware, firmware, digital signal processors, or on a specially programmed computer including a processor operating according to programmed instructions. The terms controller or processor as used herein are intended to include microprocessors, microcomputers, Application Specific Integrated Circuits (ASICs), and dedicated hardware controllers. One or more aspects of the disclosure may be embodied in computer-usable data and computer-executable instructions, such as in one or more program modules, executed by one or more computers (including monitoring modules), or other devices. Generally, program modules include routines, programs, objects, components, data structures, etc. that perform particular tasks or implement particular abstract data types when executed by a processor in a computer or other device. The computer executable instructions may be stored on a computer readable storage medium such as a hard disk, optical disk, removable storage media, solid state memory, Random Access Memory (RAM), etc. As will be appreciated by one of skill in the art, the functionality of the program modules may be combined or distributed as desired in various aspects. In addition, the functionality may be embodied in whole or in part in firmware or hardware equivalents such as integrated circuits, FPGA, and the like. Particular data structures may be used to more effectively implement one or more aspects of the disclosure, and such data structures are contemplated within the scope of computer executable instructions and computer-usable data described herein.

The disclosed aspects may be implemented, in some cases, in hardware, firmware, software, or any combination thereof. The disclosed aspects may also be implemented as instructions carried by or stored on one or more or computer-readable storage media, which may be read and executed by one or more processors. Such instructions may be referred to as a computer program product. Computer-readable media, as discussed herein, means any media that can be accessed by a computing device. By way of example, and not limitation, computer-readable media may comprise computer storage media and communication media.

Computer storage media means any medium that can be used to store computer-readable information. By way of example, and not limitation, computer storage media may include RAM, ROM, Electrically Erasable Programmable Read-Only Memory (EEPROM), flash memory or other memory technology, Compact Disc Read Only Memory (CD-ROM), Digital Video Disc (DVD), or other optical disk storage, magnetic cassettes, magnetic tape, magnetic disk storage or other magnetic storage devices, and any other volatile or nonvolatile, removable or non-removable media implemented in any technology. Computer storage media excludes signals per se and transitory forms of signal transmission.

Communication media means any media that can be used for the communication of computer-readable information. By way of example, and not limitation, communication media may include coaxial cables, fiber-optic cables, air, or any other media suitable for the communication of electrical, optical, Radio Frequency (RF), infrared, acoustic or other types of signals.

The previously described versions of the disclosed subject matter have many advantages that were either described or would be apparent to a person of ordinary skill. Even so, these advantages or features are not required in all versions of the disclosed apparatus, systems, or methods.

Additionally, this written description makes reference to particular features. It is to be understood that the disclosure in this specification includes all possible combinations of those particular features. Where a particular feature is disclosed in the context of a particular aspect or example, that feature can also be used, to the extent possible, in the context of other aspects and examples.

Also, when reference is made in this application to a method having two or more defined steps or operations, the defined steps or operations can be carried out in any order or simultaneously, unless the context excludes those possibilities.

Although specific examples of the disclosure have been illustrated and described for purposes of illustration, it will be understood that various modifications may be made without departing from the spirit and scope of the disclosure. Accordingly, the disclosure should not be limited except as by the appended claims.

We claim:

1. An accessory device, comprising:
   a first port configured to receive, from a subject, a physiological signal of the subject and to output, to the subject, an electric shock;
   a second port configured to be removably connected to a medical device and to receive the electric shock from the medical device; and
   a shielded path between the first and second ports; and
   a processor having continual communication with the first and second ports by electrical connections that are separate or different from the shielded path, the processor configured to:
      remove, from the physiological signal, a motion artifact;
      in response to removing the motion artifact, determine that the physiological signal is indicative of a condition;
      generate a simulated signal indicative of the condition; and
      in response to determining that the physiological signal is indicative of the condition, cause the second port to output the simulated signal to the medical device, the simulated signal being configured to cause the medical device to output the electric shock to the subject via an electric shock path between the medical device and the subject, the electric shock path comprising the shielded path passing through the accessory device, the shielded path protecting the processor from being impacted by the electric shock as the electric shock passes from the second port, through the shielded path, and to the first port.

2. The accessory device of claim 1, wherein the physiological signal comprises an electrocardiogram signal, an impedance signal, a capnography signal, a plethysmography signal, an oximetry signal, a pressure signal, a temperature signal, or a cardiopulmonary resuscitation feedback signal.

3. The accessory device of claim 1, wherein the motion artifact comprises a chest compression artifact or a ventilation artifact.

4. The accessory device of claim 1, further comprising: electrodes coupled to the first port.

5. The accessory device of claim 1, wherein causing the second port to output the simulated signal further comprises causing the second port to output a deterministic signal as the simulated signal.

6. The accessory device of claim 1, further comprising:
   a first circuit comprising the processor, the first port, and the second port;
   a second circuit comprising the first port and the second port; and
   a switch configured to selectively disconnect the first circuit.

7. The accessory device of claim 1, wherein the accessory device is further configured to receive the electric shock as a therapy signal from the medical device and to route the electric shock through the second port, then the shielded path, and then the first port, and then to the subject.

8. The accessory device of claim 1, wherein the processor is configured to:
   repeatedly exchange communication signals with the first and second ports by the electrical connections; and
   filter the physiological signal from among the communication signals.

9. A method, comprising:
   receiving, by a first port connected to a shielded path between the first port and a second port of an accessory device, a physiological signal from a subject;
   removing, by a processor having continual communication with the first and second ports via a separate or different signal path from the shielded path, a motion artifact from the physiological signal;
   in response to removing the motion artifact, determining that the physiological signal is indicative of a condition;
   generating a simulated signal indicative of the condition;
   in response to determining that the physiological signal is indicative of the condition, outputting, by a second port of the accessory device, the simulated signal indicative of the condition to a medical device;
   in response to outputting the simulated signal indicative of the condition to the medical device, receiving an electric shock from the medical device; and
   outputting, by the first port, the electric shock to the subject, the electric shock being routed to the subject via an electric shock path between the medical device and the subject, the electric shock path comprising the shielded path passing through the accessory device, the shielded path protecting the processor from being impacted by the electric shock as the electric shock passes from the second port, through the shielded path, and to the first port.

10. The method of claim 9, wherein the accessory device is configured to receive the electric shock as a therapy signal from the medical device and to route the electric shock through the second port, the shielded path, and the first port, and to the subject.

11. The method of claim 9, wherein the physiological signal comprises an electrocardiogram signal, an impedance signal, a capnography signal, a plethysmography signal, an oximetry signal, a pressure signal, a temperature signal, or a cardiopulmonary resuscitation feedback signal.

12. The method of claim 9, wherein the motion artifact comprises a chest compression artifact or a ventilation artifact.

13. A system, comprising:
an accessory device comprising:
- a first port configured to receive, from a subject receiving chest compressions, an electrical signal indicative of an electrocardiogram (ECG) of the subject;
- a second port;
- a shielded path between the first and second ports; and
- a processor having continual communication with the first and second ports via a separate or different signal path from the shielded path, the processor configured to:
  - remove, from the ECG, an artifact associated with the chest compressions;
  - determine, by analyzing the ECG, that the ECG is indicative of ventricular fibrillation (VF);
  - generate a simulated ECG indicative of VF; and
  - cause the second port to output the simulated ECG indicative of VF; and a defibrillator removably connected to the second port and configured to:
- receive the simulated ECG indicative of VF; and
- in response to receiving the simulated ECG indicative of VF and to being stimulated by the simulated ECG to output an electric shock, output the electric shock to the subject via an electric shock path between the defibrillator and the subject, the electric shock path comprising the shielded path passing through the accessory device, the shielded path protecting the processor from being impacted by the electric shock as the electric shock passes from the second port, through the shielded path, and to the first port.

14. The system of claim 13, wherein the first port is further configured to receive the electrical signal, the electrical signal being indicative of an impedance of the subject, and
wherein the processor is configured to remove, from the ECG, the artifact associated with the chest compressions by analyzing the impedance.

15. The system of claim 13, wherein the second port of the accessory device is configured to be connected to the defibrillator by a wired connection.

16. The system of claim 13, wherein the accessory device further comprises:
electrodes coupled to the first port.

17. The system of claim 13, wherein the accessory device comprises:
- a first circuit comprising the processor, the first port, and the second port;
- a second circuit comprising the first port and the second port; and
- a switch configured to selectively disconnect the first circuit.

18. The system of claim 13, wherein the accessory device further comprises:
memory configured to store data indicative of the ECG.

19. The system of claim 13, wherein the processor is configured to remove, from the ECG, a ventilation artifact.

20. The system of claim 13, wherein the processor is configured to:
- repeatedly exchange communication signals with the first and second ports by the electrical connections, and
- filter the electrical signal from among the communication signals.

* * * * *